United States Patent [19]

Israelsen

[11] Patent Number: 5,545,224
[45] Date of Patent: Aug. 13, 1996

[54] CRANIAL IMPLANT HAIRPIECE RETAINER SYSTEM

[76] Inventor: L. Douglas Israelsen, 3907 Alta Approach, Sandy, Utah 84092

[21] Appl. No.: 504,535

[22] Filed: Jul. 20, 1995

[51] Int. Cl.$^6$ ........................................ A61F 2/10
[52] U.S. Cl. ................................ 623/15; 606/187
[58] Field of Search ................ 623/11, 15; 606/133, 606/187; 128/898

[56] References Cited

U.S. PATENT DOCUMENTS

| | | | |
|---|---|---|---|
| 3,694,819 | 10/1972 | Meyer | 623/15 |
| 3,811,425 | 5/1974 | Widdifield | 623/15 X |
| 3,858,247 | 1/1975 | Bauman | 623/15 |
| 3,942,195 | 3/1976 | Bauman | 623/15 |
| 4,969,903 | 11/1990 | Valle | 623/15 |

Primary Examiner—Mary Beth Jones
Attorney, Agent, or Firm—Knobbe, Martens, Olson & Bear

[57] ABSTRACT

A hairpiece system, comprising (a) at least one fixation assembly, comprising a cranial implant having a threaded portion at a first end thereof and a head at a second end thereof, a percutaneous attachment adapter removably attached to the second end of the implant and having an outer end extending away from the implant, and a releasable connector attached to the attachment adapter, and (b) a hairpiece having at least one fixation assembly attached thereto through the first connector of the assembly.

7 Claims, 6 Drawing Sheets

CRANIAL IMPLANT HAIRPIECE RETAINER SYSTEM

FIELD OF THE INVENTION

The present invention relates to a hairpiece retainer system utilizes an osseointegrating threaded cranial implant for anchoring a hairpiece. Also disclosed is a method for attaching the hairpiece using the cranial implant.

BACKGROUND OF THE INVENTION

Much effort has been devoted to the field of hair replacement. Loss of hair creates a major difference in a person's appearance. Some of the many techniques for addressing hair loss include pharmaceutical treatments (e.g., Minoxidil); hair transplants; and hairpieces. In many instances, the pharmaceutical treatments and hair transplants are not satisfactory. Accordingly, one is left with the option of using a hairpiece and the attendant problem of securing the hairpiece to the head. This is not a trivial undertaking.

Hair weaving techniques have long been used to attach hairpieces. Such weaving techniques are often unstable due to lack of native hair. Moreover, it is a temporary procedure because the underlying hair grows out. Many surgical methods have also been proposed. However, such methods all have drawbacks of one type or another.

U.S. Pat. No. 4,050,100 to Barry discloses implantation of a tube in the scape. A wire extending through the tube is used to attach a hairpiece. Bauman, U.S. Pat. No. 4,372,317, discloses surgical formation of an epithelium-lined tunnel in the scalp. A flange or tab located in the tunnel is used to secure the hairpiece.

Tofield, in U.S. Pat. No. 4,676,802, discloses use of a skin graft to form a pouch in the scalp, in which a securing device is placed.

One of the difficulties with these techniques relates to the stresses applied to the scalp by the hairpiece. A pouch or tube implanted in the scalp can move, because it is attached only to skin. Movement during sleep can apply stress to the anchors, which can be quite painful. In some cases, the scalp can be torn if unexpected stress is applied to the hairpiece. Moreover, pouches and tubes must be periodically cleaned to prevent infection. Cleaning of such fixation systems is a frequent necessary and is relatively difficult.

Some of these problems are addressed by Whiddifield, U.S. Pat. No. 3,811,245. This patent discloses a permanently implanted anchor inserted underneath the scalp between the periosteum and the skull, with a tip permanently protruding from the scalp. Although such an anchor could provide a rigid attachment point for a hairpiece, eliminating the pain, pulling, and tearing that could occur with other systems, it is a permanent system. Tissue and even bone are said to attach to the implant, which always protrudes through the scalp, even when one no longer desires to wear a hairpiece. Removal of the anchor can be traumatic or impossible.

Accordingly, an object of the present invention is to provide a rigid, skull-mounted implant to which a hairpiece can be readily attached and removed.

Another object of the present invention is to provide a system for repainting a hairpiece that provides the advantage of solid installation, but also permits removal of the portion of the system extending through the scalp if the system is no longer desired.

Yet another object of the present invention is to provide a hairpiece retaining system that eliminates the pain and discomfort of retaining devices attached only to the scalp.

Still another object of the present invention is to provide a hairpiece retaining system from which the hairpiece is readily removable for cleaning or replacement.

Additional objects, features, and advantages of the present invention will be apparent from the following description.

SUMMARY OF THE INVENTION

The present invention provides an implant permanently fixed to the skull, a transepithelial attachment adapter that can be removed if desired (allowing the implant to be hidden by the scalp), and a releasable connector for connecting the hairpiece to the adapter. Because the adapter is preferably flush with the scalp and is rigidly fixed to the skull, the discomfort and injury associated with prior art fixation systems has been overcome. Moreover, although the implant is permanent, it can easily be hidden beneath the scalp by removing the attachment adapter if its use for attaching a hairpiece is discontinued.

More specifically, one aspect of the present invention relates to a hairpiece system, comprising (a) at least one fixation assembly, comprising a cranial implant having a threaded portion at a first end thereof and a head at a second end thereof, a percutaneous attachment adapter removably attached to the second end of the implant and having an outer end extending away from the implant, and a releasable connector attached to the attachment adapter, and (b) a hairpiece having at least one fixation assembly attached thereto through the first connector of the assembly. Preferably, the system includes a plurality of the fixation assemblies attached to the hairpiece.

The attachment adapter may be a cylinder and the outer end of the adapter is preferably an open end. In one embodiment, the cranial implant has a threaded opening in the head thereof, and the system further includes a screw in the threaded opening attaching the attachment adapter to the implant. The releasable connector is attached to the attachment adapter using a variety of attachments, including a snap attachment wherein the attachment adapter includes a recess and the releasable connector includes a detent (such as a spring-loaded ball) adapted to fit into the recess. Alternatively, the detent can be on the attachment adapter and the releasable connector can include a matching recess. In another embodiment, the releasable connector is screwed into the attachment adapter.

Another aspect of the present invention relates to a method for attaching a hairpiece to a human head, comprising the steps of implanting a plurality of threaded cranial implants into the skull, connecting to each of the implants a removable attachment adapter extending from the cranial implant through the scalp, and releasably attaching a hairpiece to the attachment adapters. The method can also include the step after the implanting step but before the connecting step of closing the scalp over the implant until osseointegration occurs, and then forming an opening in the scalp to expose the implant. Preferably, the attachment adapter is approximately flush with the scalp. The method can further include the step of disconnecting the attachment adapter from the implant and closing the scalp to hide the implant. Another method step of the present invention is disconnecting the hairpiece from the attachment adapter by separating the attachment adapter and the releasable connector, such as by unsnapping or unscrewing.

DETAILED DESCRIPTION OF THE INVENTION

The present invention provides the permanency of a skull-mounted anchor with the ease of removal of scalp-mounted anchors. Additionally, various connecting means are provided for easily connecting a hairpiece to and removing a hairpiece from the implanted anchor.

Figure 1:
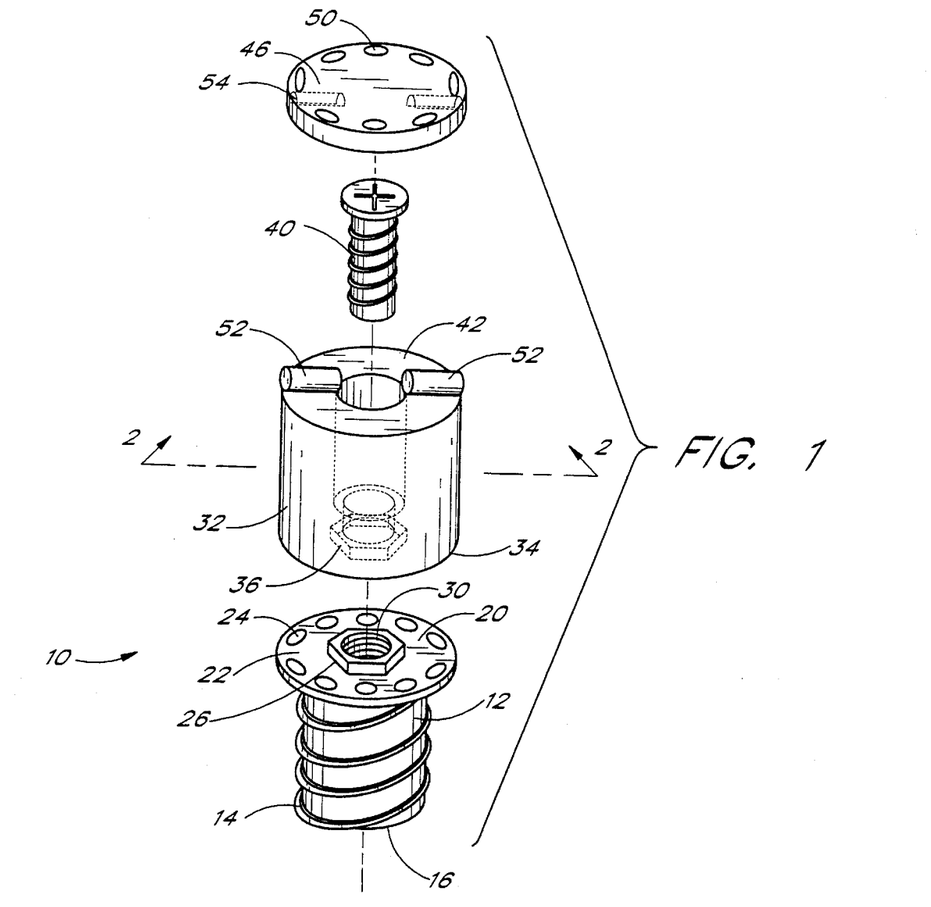
FIG. 1 is an exploded view of one embodiment of the hairpiece retaining system of the present invention.
Figure 2:
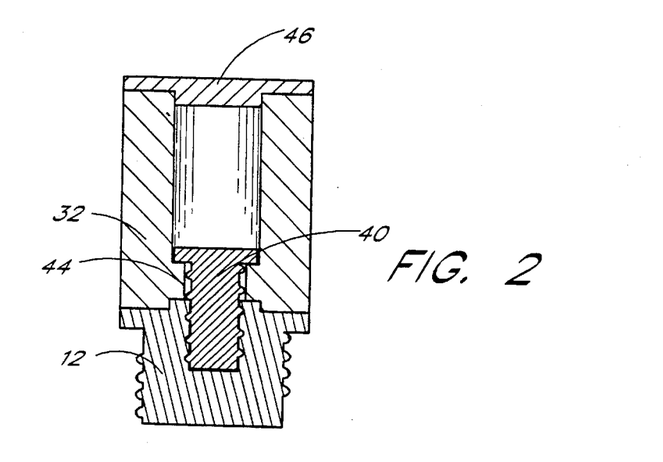
FIG. 2 is a cross-section of the system of FIG. 1, taken along the line 2—2, and illustrating the components in assembled form.

With reference now to FIG. 1, the hairpiece retaining system of the present invention includes a fixation assembly 10, shown in assembled form in cross-section in FIG. 2. Other variations of the fixation assembly 10 are shown in FIGS. 3–8.

In each of these embodiments, the fixation assembly 10 includes a cranial implant 12 for implantation into the skull. The cranial implant 12 is preferably threaded with external threads 14 for gripping the skull until osseointegration occurs. The cranial implant 12 is preferably cylindrical in shape, and may advantageously be made of a biocompatible metal. Titanium implants are particularly preferred due to their biocompatability and ready osseointegration after implantation.

The threads 14 are formed on a first end 16 of the implant 12. At the second end 20 of the implant 12 there is advantageously provided a depth-limiting collar 22. The depth-limiting collar 22 is analogous to a thin, flat head on a screw, and serves the same purpose: it prevents the implant 12 from being threaded too far into the skull during the implantation procedure. The depth-limiting collar 22 preferably comprises a flat disk attached to or formed integrally with the second end 20 of the cranial implant 12. The depth-limiting collar 22 may have a plurality of holes 24 formed therein, to promote osseous ingrowth and fixation.

To facilitate insertion of the implant 12, a nut or other gripping member 26 is advantageously provided at the second end. The nut 26 permits the surgeon to apply rotational force to the implant 12 in order to thread the implant 12 into the skull.

In the illustrated embodiment, the implant 12 also includes an axial bore 30 extending from the second end 20 toward the first end 16 of the implant 12. However, the axial bore 30 does not extend all the way to the first end 16. Preferably, the axial bore is threaded and extends through the nut 26. When the cranial implant 12 is in the form of a cylinder, the axial bore 30 runs along the axis of the cylinder.

Suitable cranial implants 12 of the type described in FIG. 1 are available from Nobel Pharma USA, Inc., Chicago, Ill., under the product designation SEC001 and SEC002. These commercially available implants are made of titanium and are 3.75 mm in diameter and 3 mm or 4 mm long.

The fixation assembly 10 also includes a percutaneous attachment adapter that is removably attached to the second end 20 of the cranial implant 12. The attachment adapter 32 is preferably a cylinder having an axial bore therethrough. The inner end 34 of the attachment adapter 32 abuts the depth-limiting collar 22 of the cranial implant 12. A recess 36, shown in phantom in FIG. 1, may advantageously be provided at the inner end 34 of the attachment adapter 32 for receiving the nut 26 when the attachment adapter 32 is abutted against the second end 20 of the cranial implant 12. When the cranial implant 12 is fixed in the skull, the recess 36 thus prevents rotation of the attachment adapter 32.

Although the attachment adapter 32 may be attached to the cranial implant 12 using any suitable means, a preferred technique utilizes a threaded screw 40 extending from the outer end 42 of the attachment adapter 32 into the bore of the attachment adapter 32 and into the threaded axial bore 30 of the cranial implant 12. As shown in more detail in FIG. 2, the bore through the center of the attachment adapter 32 includes a lip 44 against which the screw 40 is tightened to secure the attachment adapter 32 to the cranial implant 12.

The attachment adapter 32 may be made of any suitable biocompatible transepithelial material. Titanium is preferred; however, stainless steel or a biocompatible polymer, such as silicone, polytetrafluoroethylene, and the like, may also be used. The attachment adapter 32 may also include a coating thereon to facilitate epithelial attachment thereto.

The fixation assembly 10 further includes a releasable connector 46 for attachment to the attachment adapter 32. The releasable connector 46 further includes means, such as holes 50, for permitting attachment of the releasable connector 46 to a hairpiece. The holes 50, of course, can be replaced with virtually any other suitable attachment mechanism, such as a snap, threads, nuts, bolts, screws, adhesives, and the like.

The various illustrated embodiments of the fixation assembly 10 differ in the mechanism by which the releasable connector 46 is attached to the attachment adaptor 32. In FIG. 1, for example, a pair of cylinders 52 are provided at the outer end 42 of the attachment adapter 32. These cylinders 52 are situated orthogonal to the axis of the attachment adapter 32. The releasable connector 46, in turn, is provided with matching recesses 54, shown in phantom in FIG. 1. In this embodiment, the releasable connector 46 is formed of resilient material. The recesses 54 define somewhat more than 180° of cylindrical art, so that the connector 46 in FIG. 1 can snap over the cylinders 52, releasably retaining the cylinders 52 in the matching recesses 54. In this manner, the connector 46 is securely retained the attachment adapter 32, but can be easily separated therefrom by application of an appropriate force.

Figure 3:
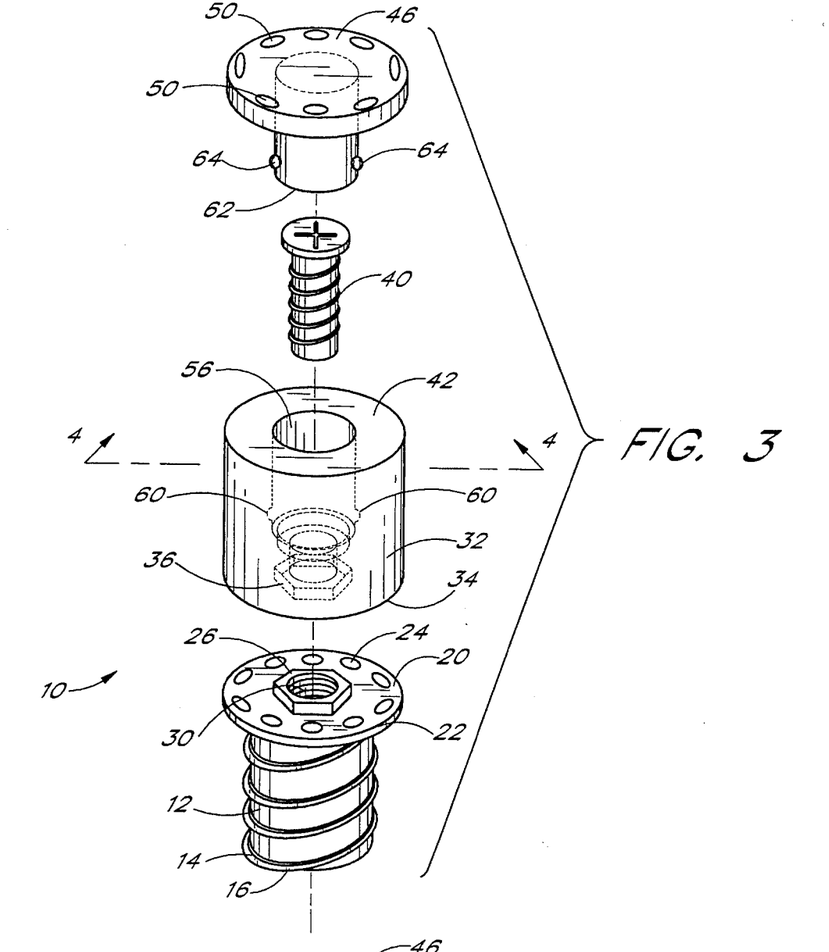
FIG. 3 is an exploded view of a second embodiment of the hairpiece retaining system of the present invention.

FIG. 3 corresponds to the fixation assembly of FIG. 1, with differences in the connection between the attachment adapter 32 and the releasable connector 46. In the illustrated embodiment, the attachment adapter 32 has an axial hole 56 extending from the outer end 42 through the attachment adapter 32 to the inner end 34. The axial hole 56 includes a pair of recesses 60 shown in phantom in FIG. 3.

The releasable connector 46 has a cylindrical portion 62 that is extends downwardly into the axial hole 56 in the attachment adapter 32. The cylindrical portion 62 of the releasable connector 46 further comprises a pair of detents that fit into the recesses 62 in a releasable manner. The detents 64 may, for example, be spring loaded balls as illustrated best in FIG. 4.

The arrangement illustrated in FIG. 3 permits the releasable connector 46 to securely engage the attachment adapter 32, yet at the same time permits ready separation of these elements for removal of a hairpiece attached to the releasable connector 46.

Figures 5, 6:
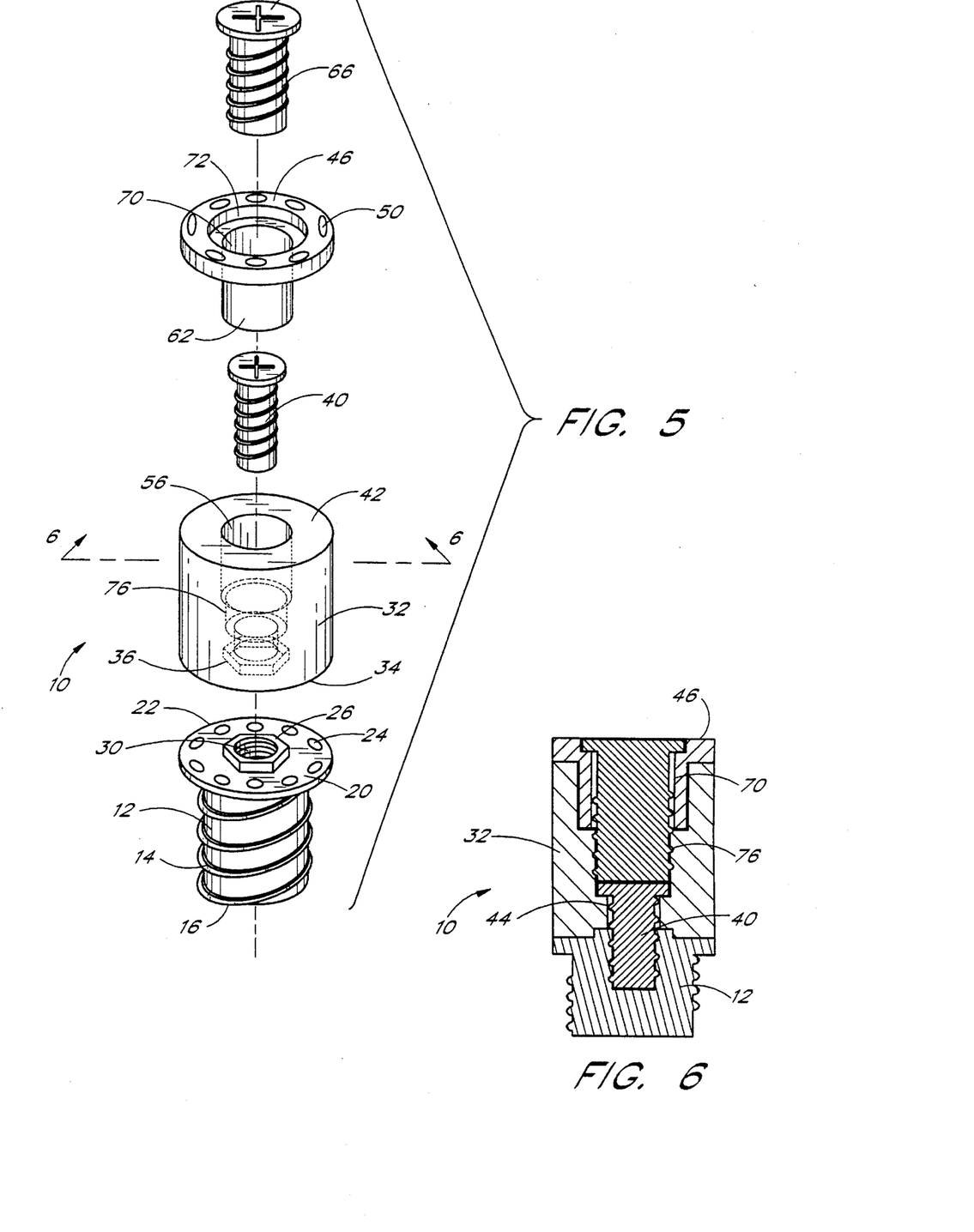
FIG. 5 is an exploded view of yet another embodiment of the hairpiece retainer system of the present invention.
FIG. 6 is an assembled view, in cross-section, taken along the line 6—6 in FIG. 5.

Yet another embodiment of the fixation assembly 10 is illustrated in FIGS. 5 and 6. In this embodiment, the releasable connector 46 is held to the outer end 42 of the attachment adapter 32 by means of a connector screw 66.

As shown in FIG. 5, the releasable connector 46 includes a cylindrical portion 62 adapted to fit into the axial hole 56 of the attachment adapter 32. The releasable connector 46 has a center bore 70 extending axially through the cylindrical portion 62. The center bore 70 is sufficiently wide to accommodate the connector screw 66, and is flared at the outer end 72 of the releasable connector 46 to accommodate the head 74 of the connector screw 66, so that the head 74 can sit flush with the outer end 72 of the releasable connector 46, as illustrated in FIG. 6.

In this embodiment, the axial hole 56 in the attachment adapter 32 has a threaded portion 76 near the outer end 42 of the attachment adapter 32 to receive the threads of the connector screw 66. As illustrated in FIG. 6, when assembled, the fixation assembly 10 is held together with two screws: the screw 40 connecting the attachment adapter 32 to the implant 12, and the connector screw 66 connecting the releasable connector 46 to the attachment adapter 32.

Figure 7:
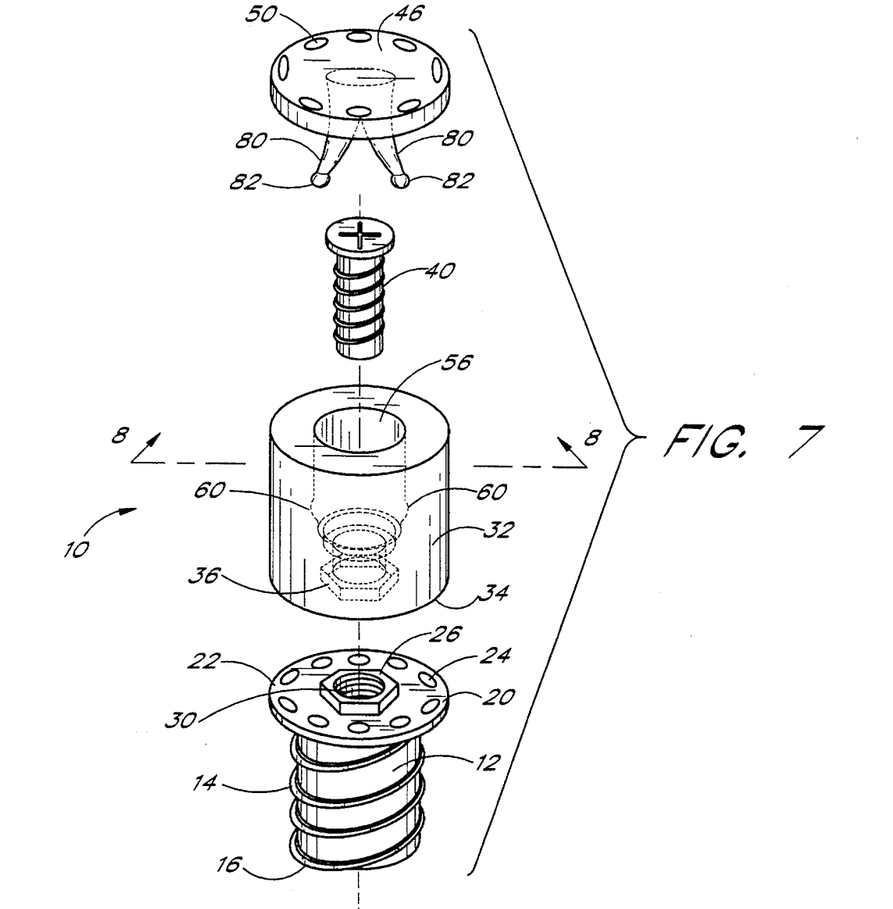
FIG. 7 is an exploded view of still another embodiment of the retainer system of the present invention.
Figure 8:
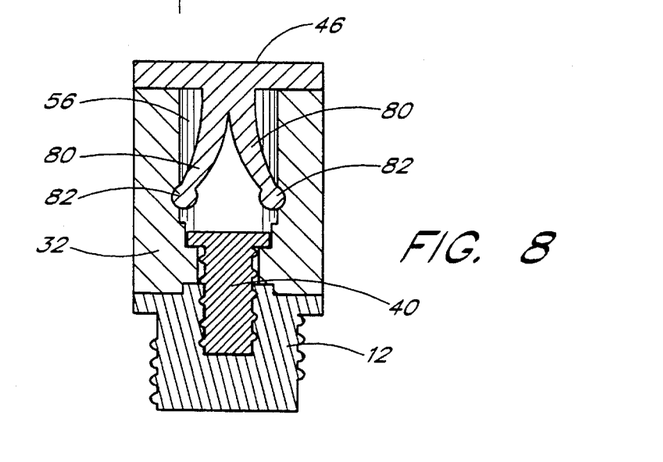
FIG. 8 is a cross-section taken along the line 8—8 in FIG. 7, showing the hairpiece retainer system in assembled form.

Still another embodiment of the present invention is illustrated in FIGS. 7 and 8. In these embodiments, the releasable connector 46 is disk-shaped, with a pair of flexible tangs 80 that extend downwardly into the axial hole 56 of the attachment adapter 46 to engage a pair of recesses 60 with detents 82 in the form of balls at the end of the tangs 80. The tangs 80 are preferably formed of thermoplastic material or other flexible polymer, although flexible metal may also be used. In use, the tangs 80 are inserted into the axial hole 56 of the attachment adapter 32. The axial hole 56 is not quite as wide as the balls 82 on the tangs 80, so that the tangs 80 must be flexed toward each other during insertion. When the tangs 80 are fully inserted into the axial hole 56, the detents 82 snap into the recesses 60, securely holding the releasable connector 46 in place.

FIGS. 1–8 illustrate a variety of possible connections between the attachment adapter 32 and the releasable connector 46. It will be appreciated, however, that numerous other connections may be substituted for those illustrative embodiments. For example, conventional hook-and-pile connectors can be used, as can all manner of latches, snaps, hooks, and the like.

Figure 9:
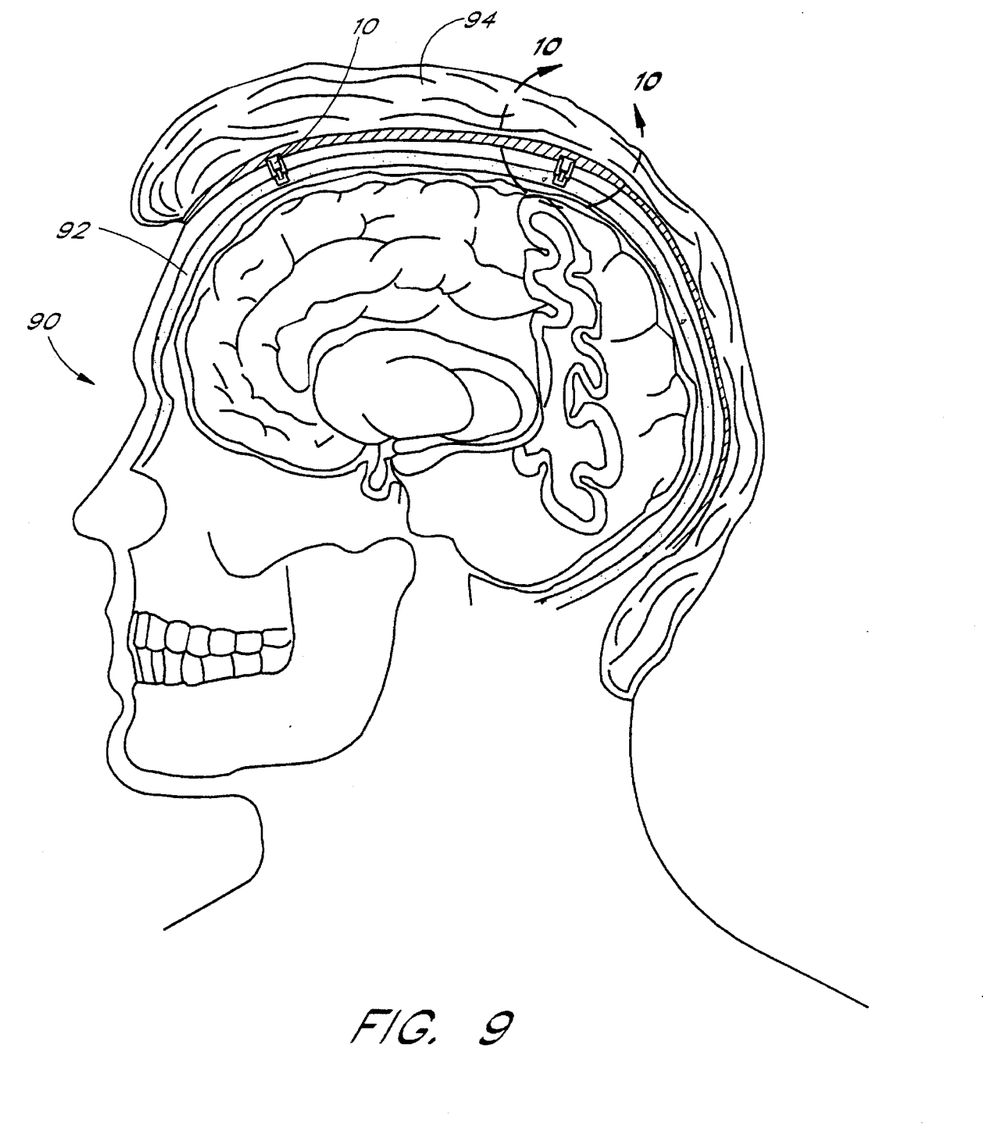
FIG. 9 is a schematic, cross-sectional view of the human head, showing the hairpiece retainer of the present invention attached thereto and securing a hairpiece in place.

FIG. 9 is a schematic diagram of the human head 90 in cross-section, showing the fixation assembly 10 secured to the skull 92, and holding a hairpiece 94 to the head 90.

Figure 4:
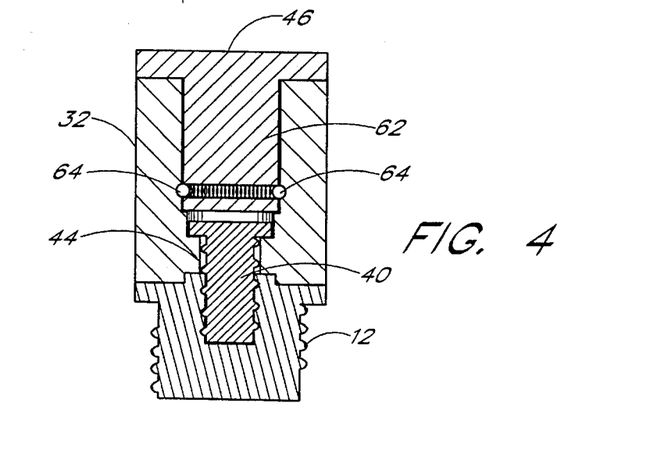
FIG. 4 is a cross-section of the system of FIG. 3, taken along the line 4—4, and showing the system in assembled form.
Figure 10:
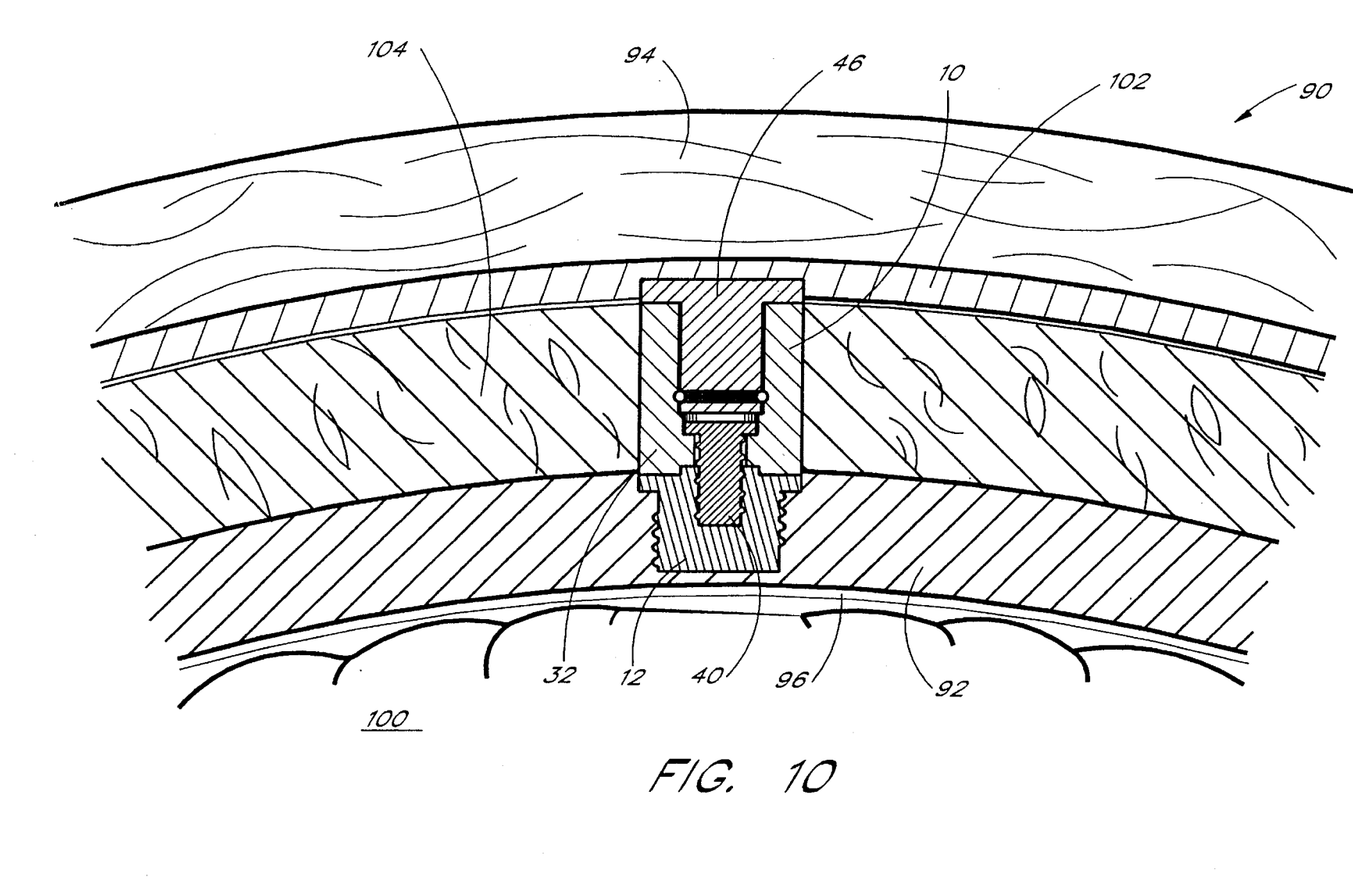
FIG. 10 is a detail of the area 10—10 in FIG. 9, showing a close-up view of one retainer of the claimed system.

With reference now to FIG. 10, an enlarged portion of FIG. 9, one can see the fixation assembly 10 of FIG. 4 holding a hairpiece 94 to the head 90. Specifically, the cranial implant 12 is threaded into the skull 92 to a depth that does not completely penetrate the skull 92. This avoids impingement upon the dura mater 96 and the brain 100.

The attachment adapter 32 is secured to the implant 12 by means of the screw 40. The releasable connector 46 is snapped into the attachment adapter 32 and is also securely fastened to the base 102 of the hairpiece 94 by any suitable connection.

The attachment adapter 32 is a transepithelial adapter, in that it extends through the scalp 104 (shown in enlarged form for better detail). In a preferred embodiment, the attachment adapter 32 is flush with the scalp, or extends only a small distance, e.g., 1 mm, 2 mm, 3 mm, or 4 mm. It will be appreciated that an important advantage of the present invention is that the implanted fixation mechanism can be made to extend only a minimal distance beyond the scalp, and that connection between the attachment adapter 32 and the can occur internal to the attachment adapter 32, below the level of the scalp. In one embodiment, the attachment adapter 32 is flesh colored. In another, a flesh colored cap is provided (which may, for example, simply be a flesh colored connector 46) for use when no hairpiece is in place.

As illustrated in FIG. 9, a plurality of fixation assemblies 10 may advantageously be used to secure the hairpiece 94 to the head 90. Specifically, 2, 3, 4, 5, 6, or more fixation assemblies 10 may be used to secure a single hairpiece.

The method for installation of the fixation assemblies 10 is as follows: first, an incision is made in the scalp 104 (and the periosteum) to expose the skull 92. A drill with a depth-limiting stop is used to drill an appropriately-sized hole in the skull 92 using gentle surgical techniques and profuse irrigation with salt solution to avoid tissue trauma. The hole is then tapped for the threads 14 of the cranial implant 12, and the implant 12 is threaded into the hole in the skull using the nut 26. The axial bore 30 is plugged with an appropriate threaded plug or cover screw (not shown), and the periosteum and scalp 104 are then sutured in place over the cranial implant 12. The implant 12 is left undisturbed for a period of approximately 2–4 months, while osseointegration occurs.

Using a punch blade the approximate diameter of the attachment adapter, holes are cut through the scalp over each of the implants. The threaded plugs are removed from the axial bore 30, and the attachment adapter 32 is connected to the implant using the screw 40. After the incision has healed, the releasable connector and the attached hairpiece can be connected to the attachment adapters.

The attachment adapter can be easily removed by removing the screw 40 and suturing the scalp to close the relatively small (3–4 mm) hole. Thus, although the implant is permanently fixed in the skull, it is invisible once the attachment adapter has been removed.

Although the present invention has been described in the context of certain preferred embodiments, it is recognized that numerous variations encompassing the spirit of the invention will be apparent to those of skill in the art. Accordingly, it is intended that the scope of the present invention be measured by the claims that follow, and lawful equivalents thereof.

What is claimed is:

1. A method for attaching a hairpiece to a human head, comprising the steps of:

implanting a plurality of threaded cranial implants into the skull;

connecting to each of said implants a removable attachment adapter extending from the cranial implant through the scalp; and releasably attaching a hairpiece to said attachment adapters.

2. The method of claim 1, further comprising the step after said implanting step but before said connecting step of closing the scalp over the implant until osseointegration occurs; and then forming an opening in the scalp to expose the implant.

3. The method of claim 1, wherein the attachment adapter is approximately flush with the scalp.

4. The method of claim 1, further comprising the step of disconnecting the attachment adapter from the implant and closing the scalp to hide the implant.

5. The method of claim 1, wherein a releasable connector connects the hairpiece to the attachment adapter, further comprising the step of disconnecting the hairpiece from the attachment adapter by separating the attachment adapter and the releasable connector.

6. The method of claim 5, wherein said disconnecting step comprises unsnapping the releasable connector from the attachment adapter.

7. The method of claim 1, wherein said step of attaching the hairpiece to the attachment adapter comprises inserting a releasable connector into the inside of the attachment adapter below the level of the scalp.

\* \* \* \* \*